United States Patent
Schalhoub et al.

(10) Patent No.: US 9,357,765 B2
(45) Date of Patent: Jun. 7, 2016

(54) HEPARAIN-BULKING AGENT COMPOSITIONS AND METHODS THEREOF

(71) Applicant: Smiths Medical ASD, Inc., Rockland, MA (US)

(72) Inventors: Kenneth G. Schalhoub, Keene, NH (US); Joseph E. Tyler, Henderson, NC (US); Quinton Farrar, Keene, NH (US)

(73) Assignee: Smiths Medical ASD, Inc., Rockland, MA (US)

( * ) Notice: Subject to any disclaimer, the term of this patent is extended or adjusted under 35 U.S.C. 154(b) by 172 days.

(21) Appl. No.: 13/827,658

(22) Filed: Mar. 14, 2013

(65) Prior Publication Data

US 2013/0260363 A1 Oct. 3, 2013

Related U.S. Application Data

(60) Provisional application No. 61/619,754, filed on Apr. 3, 2012.

(51) Int. Cl.
| | |
|---|---|
| *A01N 1/02* | (2006.01) |
| *A61L 33/00* | (2006.01) |
| *A61K 9/19* | (2006.01) |
| *A61K 31/727* | (2006.01) |
| *A61K 47/26* | (2006.01) |
| *A61K 9/14* | (2006.01) |
| *A61K 9/16* | (2006.01) |

(52) U.S. Cl.
CPC ............ *A01N 1/0226* (2013.01); *A61K 9/145* (2013.01); *A61K 9/1623* (2013.01); *A61K 9/19* (2013.01); *A61K 31/727* (2013.01); *A61K 47/26* (2013.01); *A61L 33/0011* (2013.01)

(58) Field of Classification Search
CPC ... A01N 1/0226; A01N 33/001; A61K 47/26; A61K 31/727; A61K 9/1623; A61K 9/19; A61K 9/145
See application file for complete search history.

(56) References Cited

U.S. PATENT DOCUMENTS

| | | |
|---|---|---|
| 3,988,429 A | 10/1976 | Richards et al. |
| 4,119,774 A | 10/1978 | Andersson et al. |
| 4,237,883 A | 12/1980 | Akhavi |
| 4,326,541 A | 4/1982 | Eckels |
| 4,340,589 A | 7/1982 | Uemura et al. |
| 4,479,799 A | 10/1984 | Thiel |
| 4,595,021 A | 6/1986 | Shimizu et al. |
| 4,617,941 A | 10/1986 | Ichikawa et al. |
| 4,874,742 A | 10/1989 | Ecanow et al. |
| 5,093,263 A | 3/1992 | Marlar et al. |
| 5,097,834 A | 3/1992 | Skrabal |
| 5,252,339 A | 10/1993 | Cristofori et al. |
| 5,504,011 A | 4/1996 | Gavin et al. |
| 5,888,824 A | 3/1999 | Isogawa et al. |
| 5,916,202 A | 6/1999 | Haswell |
| 6,139,878 A | 10/2000 | Summaria et al. |
| 6,159,468 A | 12/2000 | Carlson et al. |
| 6,179,819 B1 | 1/2001 | Haswell |
| 6,194,394 B1 | 2/2001 | Hawkins |
| 6,458,383 B2 | 10/2002 | Chen et al. |
| 6,655,379 B2 * | 12/2003 | Clark et al. .............. 128/203.12 |
| 2001/0024658 A1 | 9/2001 | Chen et al. |
| 2002/0192734 A1 | 12/2002 | Antignani et al. |
| 2003/0120198 A1 | 6/2003 | Barkell et al. |
| 2003/0215784 A1 | 11/2003 | Dumont et al. |
| 2005/0124965 A1 | 6/2005 | Haywood |
| 2006/0212020 A1 | 9/2006 | Rainen et al. |
| 2006/0292081 A1 | 12/2006 | Morton et al. |
| 2008/0287829 A1 | 11/2008 | Moore et al. |
| 2011/0027771 A1 | 2/2011 | Deng |

FOREIGN PATENT DOCUMENTS

| | | |
|---|---|---|
| CN | 101385739 A | 3/2009 |
| CN | 102379838 A | 3/2012 |
| EP | 0 341 291 | 11/1989 |
| EP | 0 609 794 A1 | 8/1994 |
| EP | 0 730 154 A1 | 9/1996 |
| EP | 0 820 293 B1 | 10/2002 |
| JP | 59-164722 | 12/1992 |
| JP | 2726112 | 3/1998 |
| JP | 3298098 | 7/2002 |
| JP | 3400905 B2 | 4/2003 |
| WO | WO 89/04654 | 6/1989 |
| WO | WO 01/85249 A1 | 11/2001 |
| WO | WO 02/064148 A2 | 8/2002 |
| WO | WO 03/041759 A1 | 5/2003 |
| WO | WO 03/097237 A2 | 11/2003 |
| WO | WO 2004/032750 A1 | 4/2004 |
| WO | WO 2004060344 A2 * | 7/2004 |

OTHER PUBLICATIONS

Rawat A. et al., Inhalable Large Porous Microspheres of Low Molecular Weight Heparin: In Vitro and In Vivo Evaluation, J. Control Release, 2008, vol. 128, No. 3, pp. 224-232.*

Celsus Products: a product brochure—available at the web—http://www.heparin.com/products.php; accessed online on Dec. 28, 2014, pp. 1-2.*

Landt M. et al., Interference in ionized calcium measurements by heparin salts, Clin. Chem., 1994, vol. 40, No. 4, pp. 565-570.*

Shur J. et al., the Spray Drying of Unfractionated Heparin: Optimization of the Operating Parameters, Drug Development and Industrial Pharmacy, 2008, vol. 34, pp. 559-568.*

Higgins, "The use of heparin in preparing samples for blood-gas analysis", Medical Laboratory, Oct. 2007, pp. 16-1720.

(Continued)

*Primary Examiner* — Satyendra K Singh

(74) *Attorney, Agent, or Firm* — Patteson Thuente Pedersen, P.A.

(57) ABSTRACT

A free-flowing anti-coagulant powder composition, the anti-coagulant composition containing heparin and a bulking agent that is lyophilized or spray dried and ground into a powder. The powdered anti-coagulant composition can be dry filled into syringes and other blood collections systems for rapid dissolution and mixing with collected blood sample without agitation of the container. The formulation may also retain a portion of the initial moisture, which may improve the shelf life and stability of the composition.

42 Claims, 6 Drawing Sheets

(56) References Cited

OTHER PUBLICATIONS

Madiedo, "Use of Syringes Containing Dry (Lyophilized) Heparin in Sampling Blood for pH Measurement and Blood-Gas Analysis", Clinical Chemistry, 1982, vol. 28, No. 7, pp. 1727-1728.
Toffaletti, "Use of Novel Preparations of Heparin to Eliminate Interference in Ionized Calcium Measurements: Have All the Problems Been Solved?", Clinical Chemistry, 1994, vol. 40, No. 4, pp. 508-509.
PCT International Search Report for International Application No. PCT/US2013/031525 dated Jun. 26, 2013, 4 pages.
Written Opinion for International Application No. PCT/US2013/031525 dated Jun. 26, 2013, 8 pages.
International Preliminary Report on Patentability for International Application No. PCT/US2013/031525, dated Oct. 7, 2014, 1 page.
Written Opinion for International Application No. PCT/US2013/031525, dated Jun. 26, 2013, 8 pages.
Bai et al., "Inhalable Lactose-Based Dry Powder Formulations of Low Molecular Weight Heparin", Journal of Aerosol Medicine and Pulmonary Drug Delivery, vol. 23, No. 2, 2010, pp. 97-104.
Supplementary European Search Report for European Application No. 13772245.0, dated Jul. 31, 2015.

* cited by examiner

HEPARAIN-BULKING AGENT COMPOSITIONS AND METHODS THEREOF

RELATED APPLICATION

The present application claims the benefit of U.S. Provisional Application No. 61/619,754 entitled FREE FLOWING POWDERED HEPARIN BULKING AGENT FORMULATION, filed Apr. 3, 2012, which is incorporated herein in its entirety by reference.

FIELD OF THE INVENTION

The present invention is directed to a heparin-bulking agent composition, which can be used in blood collection containers as an anticoagulant. Specifically, the present invention is directed to a heparin salt such as lithium, sodium, calcium, or zinc and a bulking agent provided in formulation, which can be lyophilized or spray dried into a heparin-bulking agent composition, which can be ground into a free-flowing powder and loaded into a blood collection container, and methods and systems related thereto.

BACKGROUND OF THE INVENTION

Blood gas analysis is a commonly performed blood test used to evaluate the dissolved gas balance and acidity of a blood sample, as well as selected electrolyte levels. A blood sample is drawn from the patient into a sample container, such as syringe, and placed into a blood gas analyzer to be evaluated. Typically, the blood analyzer inserts electrodes surrounded by a semi-permeable membrane into the sample to create a potential across in the membrane drawing hydrogen ions through the membrane. The hydrogen ion activity is measured to determine the acidity of the sample. This method of the blood gas analysis, along with the analyses of other gases and/or electrolytes, requires that the blood remain in the liquid phase throughout the analysis. In addition, if the blood coagulates within the analyzer, the analyzer must be cleaned or may become damaged. As a result, an anti-coagulant, such as heparin, is normally introduced into the blood sample prior to the sample being inserted into the analyzer to prevent the blood from coagulating during testing and thereby eliminating the drawbacks associated with coagulated blood samples.

A common approach to introducing electrolyte balanced heparin into a blood sample is to first draw a liquid heparin aliquot into the syringe that is to be used to draw blood. The majority of the heparin aliquot is then expelled leaving either a small amount of liquid heparin in the syringe or a heparin coating on the internal walls of the syringe. A drawback of this approach is that actuating the syringe to draw or expel heparin can introduce air bubbles into the syringe. In addition to the health risks of introducing air bubbles into the blood stream while drawing the blood sample, any air bubbles in the blood sample can significantly alter the resulting blood gas analysis.

Another common approach is preloading a container with heparin by atomizing the liquid heparin onto the interior of the container and then subsequently drying as described in US Patent Publication No. 2003/0120198. A drawback of atomizing the heparin into a container and then subsequently drying it is that the resulting heparin composition has a glassy consistency, which makes it difficult for quick dissolution of the heparin in a blood sample. A similar drawback is that the dosage of heparin applied, which may have a varying heparin activity from production lot to lot, is limited by the surface area of the container.

Another approach to introducing heparin is to place a tablet or pledget of heparin within the container that dissolves when the blood sample is drawn into the container. This approach is described in U.S. Pat. Nos. 5,093,263 and 5,916,202. Although the dosage of heparin can be varied with this approach, the container must be agitated to dissolve and distribute the heparin throughout the sample. Another drawback is that the rate of dissolution of the heparin is limited by the surface area of the tablet or pledget. If the heparin is not effectively or quickly mixed, portions of the sample may coagulate preventing effective analysis of the blood sample. A common source of this problem is medical personnel who draw the blood sample without sufficiently agitating the container to dissolve and mix the heparin throughout the blood sample.

Thus, although heparin is commonly used as an anti-coagulant for blood gas samples, there remains a need for an anti-coagulant for blood samples with an efficient rate of dissolution. In particular, the current approaches are dependent on medical personnel sufficiently agitating the blood sample to properly dissolve the heparin throughout the blood sample. It is also always desirable to find alternative solutions to blood sample management.

SUMMARY OF THE INVENTION

The present invention is directed to a heparin-bulking agent formulation in which a heparin component is combined with one or more bulking agents, the heparin-bulking agent formulation lyophilized or spray dried and ground to provide a free-flowing powered heparin-bulking agent composition that readily dissolves in a blood sample.

In certain aspects of the present invention, the heparin component is separately lyophilized and ground to a predetermined particulate size before being combined with a bulking agent. In certain other aspects of the present invention, the heparin-bulking agent formulation is lyophilized and ground to the desired particulate size. The free flowing powdered heparin-bulking agent composition can be filled into a container, such as a blood collection container. In some other aspects of the present invention, the heparin-bulking agent formulation is spray dried into a solid mass before being ground to a desired particulate size. The free flowing powdered heparin-bulking agent composition can be filled into a container, such as a blood collection container. In some other aspects of the present invention, the heparin component and the one or more bulking agent components are combined, mixed and dissolved in solution to form the heparin-bulking agent formulation before being spray dried or lyophilized and then ground to a predetermined particulate size. In some aspects, the heparin component and the one or more bulking agent components are provided as either a solid material or in solution before being combined and/or mixed together into a solution heparin-bulking agent formulation.

In certain aspects of the present invention, the heparin-bulking agent composition in a free-flowing powder form can be filled into a container, such as a blood sample collection tube, syringe, vacuum tube, and the like. In certain aspects of the present invention, the heparin-bulking agent composition in a free-flowing powder form can be preloaded into the barrel of a syringe to mix with a blood sample as the blood sample is drawn into the barrel, whether directly from a patient or from another blood collection container. The amount of free-flowing, powdered heparin-bulking agent composition placed in the container can be varied depending on the circumstances, such as the volume of the blood sample to be taken, the container size, and the desired activity concentration of the respective heparin component. In a powder form, the heparin-bulking agent composition dissolves more rapidly than heparin coatings or tablets due to a higher surface area, thereby creating faster dissolution. In some aspects, the heparin-bulking agent composition provided in a powder form dissolves and distributes throughout the sample by virtue of the flow of the blood sample entering into the container, and without requiring agitation of the container by the medical personnel drawing the blood sample.

In certain aspects of the present invention, an anti-coagulant formulation is provided comprising a heparin component and at least one bulking agent. The bulking-agent can be non-reactive with blood enzymes and otherwise not have any effect on the clinical chemistry of the blood sample. The heparin component and the at least one bulking agent component can be provided as a solution of a heparin-bulking agent formulation. The solvent content of the heparin-bulking agent formulation is reduced by lyophilization into a heparin-bulking agent composition or spray drying into a heparin-bulking agent composition, and then the heparin-bulking agent composition can be ground into a free-flowing powder. The bulking agent provided in the heparin-bulking agent composition provides enough mass to the composition, such that after the heparin-bulking agent composition is ground to a free-flowing powder, the free-flowing powder can be filled into a container, such as a blood collection container. The free-flowing powder also readily dissolves within a blood sample as the blood sample is introduced into the sample container containing the heparin-bulking agent composition.

In certain aspects of the present invention, an anti-coagulant formulation is provided consisting of a heparin component and at least one bulking agent. The bulking agent can be non-reactive with blood enzymes and otherwise not have any effect on the clinical chemistry of the blood sample. The heparin component and the at least one bulking agent component can be provided as a solution a heparin-bulking agent formulation. The solvent content of the heparin-bulking agent formulation is reduced by lyophilization into a heparin-bulking agent composition or spray drying into a heparin-bulking agent composition, and then the heparin-bulking agent composition can be ground into a free-flowing powder. The bulking agent provided in the heparin-bulking agent composition provides enough mass to the composition, such that after the heparin-bulking agent composition is ground to a free-flowing powder, the free-flowing powder can be filled into a container, such as a blood collection container. The free-flowing powder also readily dissolves within a blood sample as the blood sample is introduced into the sample container containing the heparin-bulking agent composition.

In certain aspects of the present invention, an anti-coagulant formulation is provided consisting essentially of a heparin component and at least one bulking agent. The bulking agent can be non-reactive with blood enzymes and otherwise not have any effect on the clinical chemistry of the blood sample. The heparin component and the at least one bulking agent component can be provided as a solution of a heparin-bulking agent formulation. The solvent content of the heparin-bulking agent formulation is reduced by lyophilization into a heparin-bulking agent composition or spray drying into a heparin-bulking agent composition, and then the heparin-bulking agent composition can be ground into a free-flowing powder. The bulking agent provided in the heparin-bulking agent composition provides enough mass to the composition, such that after the heparin-bulking agent composition is ground to a free-flowing powder, the free-flowing powder can be filled into a container, such as a blood collection container. The free-flowing powder also readily dissolves within a blood sample as the blood sample is introduced into the sample container containing the heparin-bulking agent composition.

In certain aspects, the heparin component and the at least one bulking agent component are both provided as solid material components, with the heparin component, the at least one bulking agent component, and/or both components being provided in solution before being combined, mixed and dissolved in solution. In certain aspects, the heparin component is provided in solution and the at least one bulking agent component is provided as a solid material component before both components being mixed together and dissolved in solution. In certain aspects, the heparin component is provided as a solid material component and the at least one bulking agent component is provided in solution before both components being mixed together and dissolved in solution. In certain aspects, the heparin component is provided as a solid material component, the at least one bulking agent component is provided as a solid material component, and a solvent is added to the heparin component and/or the at least one bulking agent component to dissolve the heparin and bulking agent components and provide a heparin-bulking agent formulation in solution. After the heparin component and the at least one bulking agent component are mixed together and dissolved in solution, the heparin-bulking agent formulation solution can be lyophilized or spray dried into a heparin-bulking agent composition. In some aspects, at least a portion of the heparin-bulking agent composition is ground into a free-flowing powder using various milling processes, including mortar and pestle, ball mill, cryogenic grinding, cryo-milling, or combinations thereof.

In certain aspects of the present invention, a range of the particle size distribution range between the $X_{10}$ and the $X_{90}$ values of the powdered heparin-bulking agent composition is less than about 320 microns, in some aspects less than about 300 microns, in some aspects less than about 270 microns, and in some other aspects less than about 250 microns.

In certain aspects of the present invention, the powdered heparin-bulking agent composition has a particle size distribution with respect to the $X_{10}$ and the $X_{90}$ values that is in the range between about 4 microns to about 400 microns, in some aspects about 8 microns to about 390 microns, in some aspects about 10 microns to about 380 microns, in some aspects about 15 microns to about 350 microns, in some aspects about 35 microns to about 280 microns, and still in some other aspects about 40 microns to about 380 microns.

In certain aspects of the present invention, the powdered heparin-bulking agent composition has a particle size distribution $X_{10}$ value of at least about 4 microns, in some aspects at least about 8 microns, in some aspects at least about 10 microns, in some aspects at least about 15 microns, in some aspects at least about 25 microns, and in some aspects at least about 30 microns. In some aspects, the powdered heparin-bulking agent composition has a particle size distribution $X_{10}$ value in the range of about 4 microns to about 40 microns, in some aspects about 4 microns to about 35 microns, in some aspects about 4 microns to about 30 microns, in some other aspects about 8 microns to about 32 microns, in some aspects about 8 microns to about 18 microns, in some aspects about 10 microns to about 18 microns, and in some other aspects about 25 microns to about 40 microns.

In certain aspects of the present invention, the powdered heparin-bulking agent has a particle size distribution $X_{90}$ value less than about 400 microns, in some aspects less than about 390 microns, in some aspects less than about 350 microns, in some aspects less than about 340 microns, in some aspects less than about 320 microns, in some aspects less than about 300 microns, in some aspects less than about 280 microns, and in some other aspects less than about 260 microns. In some aspects, the powdered heparin-bulking agent composition has a particle size distribution $X_{90}$ value in the range of about 260 microns to about 400 microns, in some aspects about 260 microns to about 280 microns, in some aspects about 280 microns to about 400 microns, in some other aspects about 280 microns to about 320 microns, in some aspects about 280 microns to about 340 microns, in some aspects about 250 microns to about 320 microns, and in some other aspects about 300 microns to about 320 microns.

In certain aspects of the present invention, the powdered heparin-bulking agent composition has a particle size distribution $X_{50}$ value in the range of about 80 microns to about 140 microns, in some aspects about 80 microns to about 100 microns, in some aspects about 85 microns to about 95 microns, in some aspects about 120 microns to about 140 microns, and in some other aspects about 125 microns to about 135 microns.

In certain aspects of the present invention, the heparin component has a known activity concentration. In certain aspects, the source of heparin may be either a dry or solution of a heparin salt, such as heparin salts chosen from lithium, sodium, calcium, or zinc. In certain aspects, the source of heparin comprises lyophilized heparin.

In certain aspects of the present invention, the bulking agent is a water soluble material. In certain aspects, the bulking agent is a water soluble material chosen from a sugar alcohol, a carbohydrate such as a monosaccharide, a disaccharide, a trisaccharide, a polysaccharide, a water-soluble polymer, or combinations thereof. In certain aspects, the bulking agent is a water soluble material chosen from a monosaccharide alcohol, a α1-1 disaccharide, a α1-6, β1-2 trisaccharide, an α1-β2 disaccharide, an β1-4 disaccharide, a polyvinylpyrollidone, or combinations thereof. In certain aspects, the bulking agent is chosen from mannitol, trehalose, raffinose, sorbitol, sucrose, lactose, polyvinylpyrollidone, and combinations thereof. In some aspects, the bulking agent is the monosaccharide alcohol D-Mannitol. In some aspects, the bulking agent is the monosaccharide D-Sorbitol. In some aspects, the bulking agent is the α1-β2 disaccharide Sucrose. In some aspects, the bulking agent is the β1-4 disaccharide α-Lactose. In some aspects, the bulking agent is the α1-1 disaccharide D(+) Trehalose dihydrate. In some aspects, the bulking agent is the α1-6, β1-2 trisaccharide D-Raffinose pentahydrate. In some aspects, the bulking agent is a polyvinylpyrollidone. In some aspects, the bulking agent is one or more of the monosaccharide D-Sorbitol, the α1-β2 disaccharide Sucrose, the β1-4 disaccharide α-Lactose, the α1-1 disaccharide D(+) Trehalose dehydrate, the α1-6, β1-2 trisaccharide D-Raffinose pentahydrate, and polyvinylpyrollidone.

In certain aspects of the present invention, the heparin-bulking agent formulation contains one or more additives that do not affect the activity of the heparin component or that otherwise negate any effect the heparin activity has on the analysis of a blood sample. Such additives may include a buffering agent, a stabilizer, or combinations thereof. In certain aspects, the heparin-bulking agent formulation contains calcium acetate, as heparin has an affinity for calcium that depletes a blood sample of the calcium giving false low values of the calcium content. The calcium component already loaded in the heparin composition thus allows an accurate reading of a patient blood sample to be obtained. The one or more additives may be added to the heparin component, the bulking-agent component, or to a solution of the heparin component and bulking-agent component. The one or more additives may be added as a solution or a solid material.

In certain aspects of the present invention, the heparin-bulking agent formulation is lyophilized until the moisture content of the formulation is adequately dry. In certain aspects of the present invention, the heparin-bulking agent formulation is lyophilized until the moisture content of the formulation is between about 0.5% to about 10%, in some aspects about 0.5% to about 7.5%, in some aspects about 0.5% to about 5%, in some about 0.5% to about 2.5%, and in some further aspects about 0.5% to about 1.5%. In certain aspects of the present invention, the heparin-bulking agent formulation is lyophilized until the moisture content of the formulation is less than about 10%, in some aspects less than about 7.5%, in some aspects less than about 5%, in some aspects less than about 2.5%, and in some further aspects less than about 1.5%. The heparin-bulking agent formulation is a solid after lyophilization and can be ground into a powder for dry filling, but retains a portion of the initial moisture within the formulation following the lyophilization. Surprisingly, retaining a moisture content within the heparin-bulking agent composition in the range of about 2% to about 7%, and in some aspects up to about 7%, rather than achieving the lowest possible moisture content may provide improved stability and shelf life for the heparin activity of the heparin-bulking agent composition. Specifically, the retained moisture decreases the sensitivity of the heparin activity to changing environmental conditions allowing the formulation to be stored for longer periods of time in areas with minimal or no environmental controls.

In certain aspects of the present invention, a free-flowing powder of a heparin-bulking agent composition has a shelf life up to about 5 years, in some aspects between about 1 to about 5 years, in some aspects about 1 year to about 3 years, and in other aspects at least about 4 years.

In certain aspects of the present invention, a system is provided for collecting and performing blood gas analysis, the system comprising a syringe having a barrel and a quantity of free-flowing anti-coagulant powder filled into the syringe barrel, wherein the anti-coagulant powder comprises a lyophilized heparin-bulking agent formulation into a heparin-bulking agent composition, the heparin-bulking agent composition ground into a free-flowing powder. In certain aspects, the syringe contains the desired amount of free-flowing powder to provide the desired activity concentration of the heparin for the respective system. In certain aspects, the syringe contains about 0.5 mg to about 5 mg of the free-flowing, powdered heparin-bulking agent composition, in some other aspects about 1.0 mg to about 3.0 mg, in some other aspects about 1.5 mg to about 2.0 mg, although other amounts greater or less than the foregoing ranges and sub-ranges being contemplated herein. In another aspect, the heparin-bulking agent composition within the respective system has a moisture content less than about 10%, in some aspects less than about 7.5%, in some aspects less than about 5%, in some aspects less than about 2.5%, and in some further aspects less than about 1.5%.

In certain aspects, the heparin-bulking agent composition provided as a free-flowing powder is loaded into the container in an inert gas environment to prevent moisture contamination into the container. In certain aspects, the free-flowing, powdered heparin-bulking agent composition is loaded into the container while the container is under vacuum with an inert gas. Alternatively, the container is placed under vacuum after the heparin-bulking agent composition is loaded into the container to remove any air in the container. Preventing air from entering the container or removing the air from the container prevents air bubbles in the blood sample that can disrupt or skew the blood gas analysis. In certain aspects, the container is a syringe with the free-flowing, powdered heparin-bulking agent composition loaded into the barrel of the syringe.

In certain aspects of the present invention, a method of making an anti-coagulant formulation comprises providing a source of heparin having a known activity concentration and a source of at least one bulking agent. In certain aspects, the source of heparin may be either a dry or solution of a heparin salt, such as heparin salts chosen from lithium, sodium, calcium, or zinc. In certain aspects, the source of heparin is lyophilized heparin. In certain aspects, the source of the at least one bulking agent can be provided in either a dry or solution form. The source of heparin and the source of at least one bulking agent are combined in a predetermined ratio to obtain the desired activity concentration of heparin units per milligram. The method further comprising mixing the heparin component and the at least one bulking agent in solution until the source of heparin and the source of at least one bulking agent are dissolved in solution to form a heparin-bulking agent formulation. The method also comprises lyophilizing the heparin-bulking agent formulation for an initial period, wherein the formulation has been dried into a solid heparin-bulking agent composition following the primary period. The method further comprises grinding the heparin-bulking agent composition into a powder having a predetermined particulate size. In certain aspects, the method further comprises optionally drying the ground heparin-bulking agent composition for a second period of time. In another aspect, the heparin-bulking agent formulation can be spray dried into a holding chamber to provide a heparin-bulking agent composition, which can then be ground into a free-flowing powder. Alternatively, the heparin-bulking agent formulation can be spray dried instead of being lyophilized before the heparin-bulking agent composition is ground into a free-flowing powder.

In certain aspects, the at least one bulking agent and heparin are provided in solution with a ratio of about 60% to about 97% by weight of solid content of the at least one bulking agent and about 3% to about 40% by weight of solid content of heparin, although other ratios greater or less than the foregoing ranges are contemplated herein. In certain aspects, the ratio of bulking agent to heparin solution is selected to produce about 1.5 mg of the dried, heparin-bulking agent composition in a powder form having the preferred activity concentration of heparin. The method can further comprise adding a quantity of a solvent, such as water (e.g., de-ionized water), to the heparin, bulking agent, heparin and bulking agent mixture, or heparin-bulking agent formulation to facilitate the dissolution of the bulking agent and heparin within solution.

In another aspect, the method can further comprise freezing the heparin-bulking agent formulation for a freezing period at a predetermined temperature to obtain a frozen solid. For example, without being bound by limitation herein, the mixture can be frozen for at least 8 hours at about −80° C. The method can further comprise lyophilizing the frozen heparin-bulking agent formulation within a lyophilizer having a desired product and/or shelf. The bulking agent provided in the heparin-bulking agent composition provides enough mass to the composition, such that after the heparin-bulking agent composition is ground to a free-flowing powder, the free-flowing powder can be filled into a container, such as a blood collection container. The free-flowing powder also readily dissolves within a blood sample as the blood sample is introduced into the sample container containing the heparin-bulking agent composition temperature. In another aspect, the primary drying period can last a desired drying period of time, while an optional subsequent additional drying period can also be utilized for a desired period of time.

A method of preparing a syringe, according to certain aspects of the present invention, comprises providing a syringe having a barrel and a quantity of an anti-coagulant comprising a heparin-bulking agent composition, the bulking agent chosen from mannitol, trehalose, raffinose and combinations thereof, wherein the heparin-bulking agent formulation is lyophilized into the heparin-bulking agent composition, which is ground into a free-flowing powder. The method further comprises dry-filling the free-flowing powder into the syringe barrel and sealing the barrel. In one aspect, the method can further comprise dry-filling the syringe barrel under an inert atmosphere (i.e., inert gas such as nitrogen, argon, and the like).

A method of using a syringe loaded with an anti-coagulant, according to certain aspects of the present invention, comprises providing a syringe having a barrel loaded with the anti-coagulant, a plunger and a needle, wherein the anti-coagulant comprises a free-flowing powder of a heparin-bulking agent composition, the bulking agent chosen from mannitol, trehalose, raffinose and combinations thereof. The method further comprises pulling the plunger to create a vacuum within the barrel to pull a blood sample into the barrel, wherein the flow of blood into the barrel circulates and dissolves the anti-coagulant into the blood. Alternatively, the method further comprises allowing arterial blood to fill a syringe with a pre-set plunger position, wherein the flow of blood into the barrel circulates and dissolves the anti-coagulant into the blood. The method can further comprise placing the syringe or an aliquot of the blood sample having the dissolved anti-coagulant from the syringe into a blood analyzer for analysis. Alternatively, the plunger can be actuated to expel the blood sample and anti-coagulant mixture into a sample blank that is insertable into a blood analyzer for analysis.

In certain aspects of the present invention, a blood collection container have a predetermined amount of a free-flowing powder of a heparin-bulking agent composition is capable of being dissolved within a blood sample of a patient in the blood collection container in less than about 10 seconds, in some aspects less than about 8 seconds, in some aspects less than about 6 seconds, in some aspects less than about 4 seconds, in some aspects less than about 2 seconds, in some aspects less than about 1 second, and in some other aspects about instantaneously. In certain aspects, a predetermined amount of a free-flowing powder of a heparin-bulking agent composition preloaded into a blood collection container is capable of being dissolved within a blood sample of a patient in the blood collection container in less than about 10 seconds, in some aspects less than about 8 seconds, in some aspects less than about 6 seconds, in some aspects less than about 4 seconds, in some aspects less than about 2 seconds, in some aspects less than about 1 second, and in some other aspects about instantaneously, without the need of agitating the blood collection container.

The above summary of the various representative embodiments of the invention is not intended to describe each illustrated embodiment or every implementation of the present invention. Rather, the embodiments are chosen and described so that others skilled in the art can appreciate and understand the principles and practices of the invention. The figures in the detailed description that follow more particularly exemplify these embodiments.

BRIEF DESCRIPTION OF THE DRAWINGS

The present invention can be more completely understood in consideration of the following detailed description of various embodiments of the invention in connection with the accompanying drawings, in which.

Figure 1:
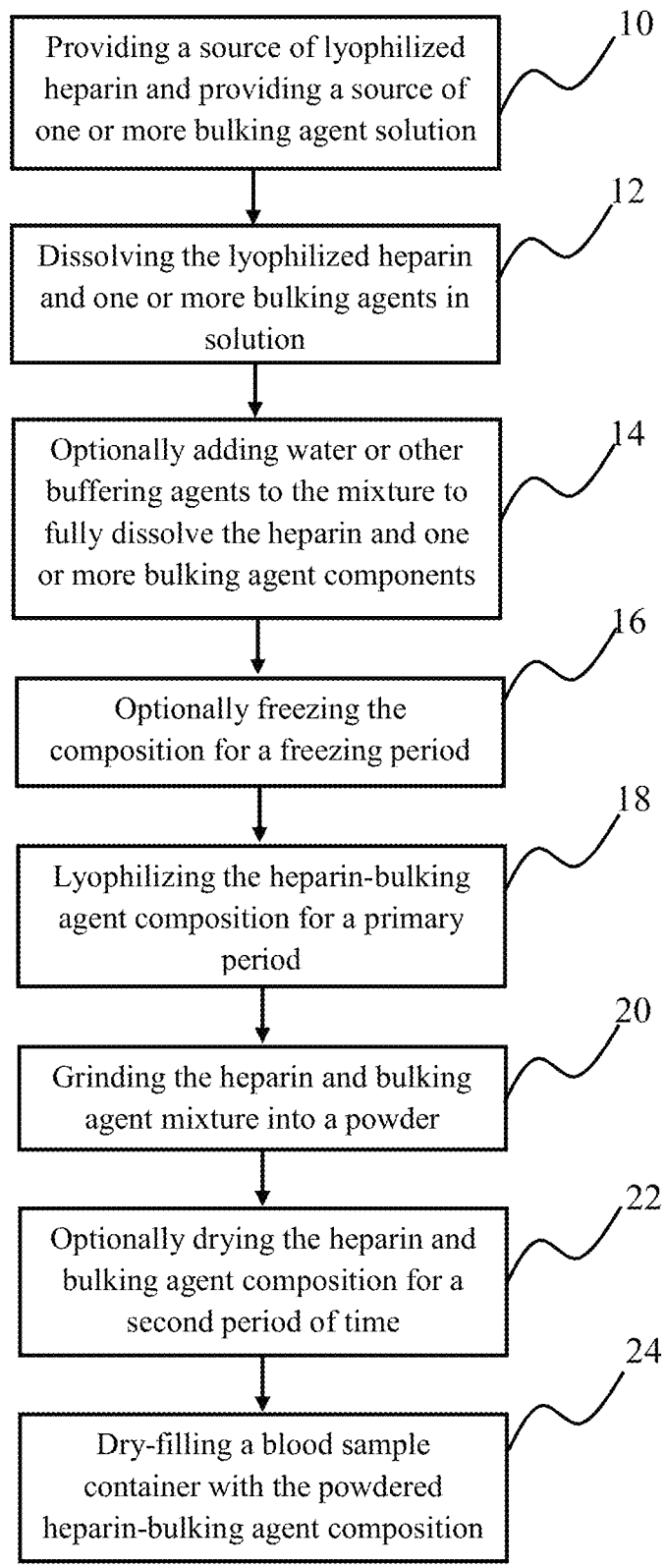
FIG. 1 is a flow diagram illustrating the formulation of an anti-coagulant using lyophilization according to certain aspects of the present invention.

While the present invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is directed to a heparin-bulking agent composition as an anti-coagulant, the composition having a heparin component and at least one bulking agent component. In some aspects, the heparin-bulking agent composition is provided in a free-flowing powder form.

In certain aspects, the heparin component may be a heparin salt such as lithium, sodium, calcium, zinc or combinations thereof. The one or more bulking agent components are selected to be non-reactive with the components within a blood sample to avoid impacting the blood gas analysis.

In certain aspects, the bulking agent component is a water soluble material. Such water soluble materials that are suitable to be a bulking agent component include a sugar alcohol, a carbohydrate such as a monosaccharide, a disaccharide, a trisaccharide, a polysaccharide, a water-soluble polymer, or combinations thereof. In certain aspects, the bulking agent can be, but is not limited to, a monosaccharide alcohol, a α1-1 disaccharide, a α1-6, β1-2 trisaccharide, an α1-β2 disaccharide, an β1-4 disaccharide, a polyvinylpyrollidone, or combinations thereof. In certain aspects, the bulking agent is chosen from mannitol, trehalose, raffinose, sorbitol, sucrose, lactose, polyvinylpyrollidone, and combinations thereof. In some aspects, the bulking agent is the monosaccharide alcohol D-Mannitol. In some aspects, the bulking agent is the monosaccharide D-Sorbitol. In some aspects, the bulking agent is the α1-β2 disaccharide Sucrose. In some aspects, the bulking agent is the β1-4 disaccharide α-Lactose. In some aspects, the bulking agent is the α1-1 disaccharide D(+) Trehalose dehydrate. In some aspects, the bulking agent is the α1-6, β1-2 trisaccharide D-Raffinose pentahydrate. In some aspects, the bulking agent is a polyvinylpyrollidone. In some aspects, the bulking agent is one or more of the monosaccharide D-Sorbitol, the α1-β2 disaccharide Sucrose, the β1-4 disaccharide α-Lactose, the α1-1 disaccharide D(+) Trehalose dehydrate, the α1-6, β1-2 trisaccharide D-Raffinose pentahydrate, and polyvinylpyrollidone.

In certain aspects of the present invention, a method of making an anti-coagulant formulation comprises providing a source of heparin with a known activity concentration and a source of at least one bulking agent. In certain aspects, the source of heparin may be either a dry or solution of a heparin salt, such as heparin salts chosen from lithium, sodium, calcium, or zinc. In certain aspects, the source of heparin comprises lyophilized heparin. In certain aspects, the source of the at least one bulking agent can be provided in either a dry or solution form. The source of heparin and the source of at least one bulking agent are combined in a predetermined ratio to obtain the desired activity concentration of heparin units per milligram. The heparin component and the at least one bulking agent are then mixed in solution until the source of heparin and the source of at least one bulking agent are dissolved in solution to form a heparin-bulking agent formulation. The heparin-bulking agent formulation is then either lyophilized or spray dried to form a heparin-bulking agent composition. The heparin-bulking agent composition can undergo further processing, such as being ground to provide the heparin-bulking agent as a free-flowing powder.

In certain aspects of the present invention, the heparin-bulking agent formulation contains one or more additives that do not substantially affect the activity of the heparin component. Such additives may include a buffering agent, a stabilizer, or combinations thereof. In certain aspects, the heparin-bulking agent formulation contains calcium acetate, as heparin has an affinity for calcium that depletes a blood sample of the calcium giving false low values of the calcium content in a blood sample of a patient. Thus, the calcium component already loaded in the heparin composition by virtue of the calcium acetate allows an accurate reading of a patient blood sample to be obtained. The one or more additives may be added to the heparin component, the bulking-agent component, or to a solution of the heparin component and bulking-agent component. The one or more additives may be added as a solution or a solid material. The one or more additives may comprise less than about 10% by total solid content of the heparin-bulking agent formulation and also the resulting heparin-bulking agent composition after lyophilization or spray drying, in some aspects less than about 8%, in some aspects less than about 6%, in some aspects less than about 4%, in some aspects less than about 2%, in some aspects less than about 1%, and in some other aspects there is no additive in the heparin-bulking agent formulation.

Figure 2:
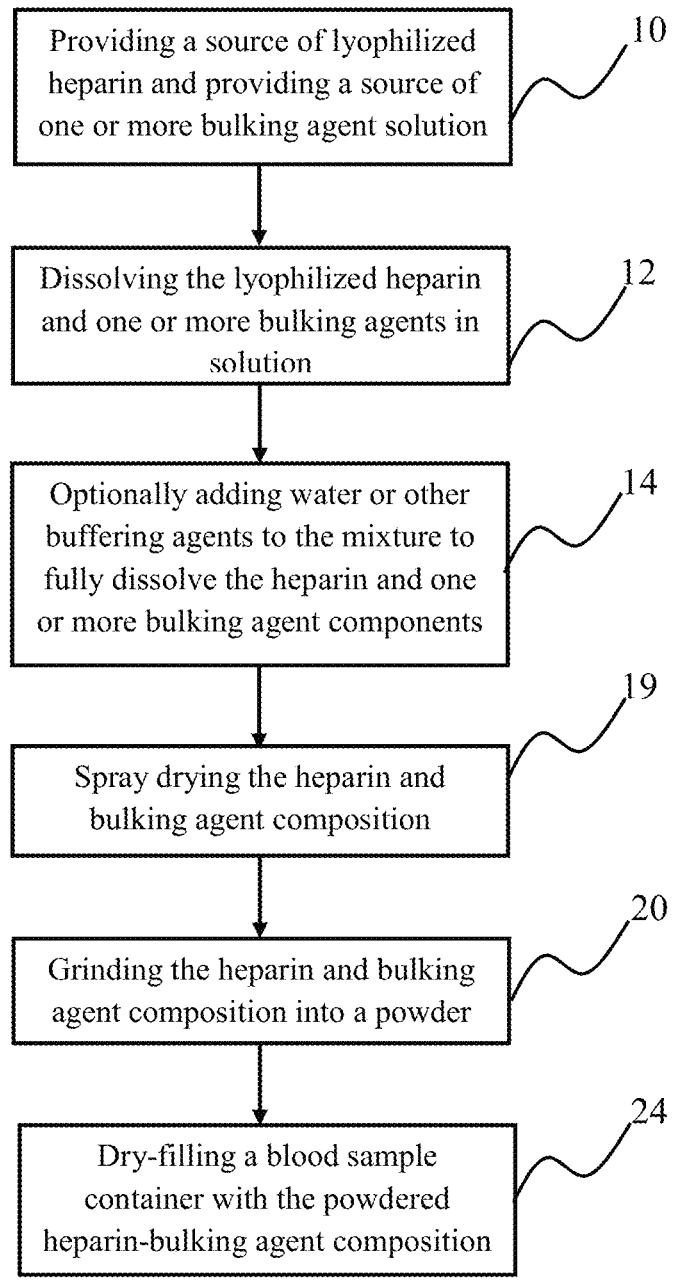
FIG. 2 is a flow diagram illustrating the formulation of an anti-coagulant using spray drying according to certain aspects of the present invention.
Figure 3:
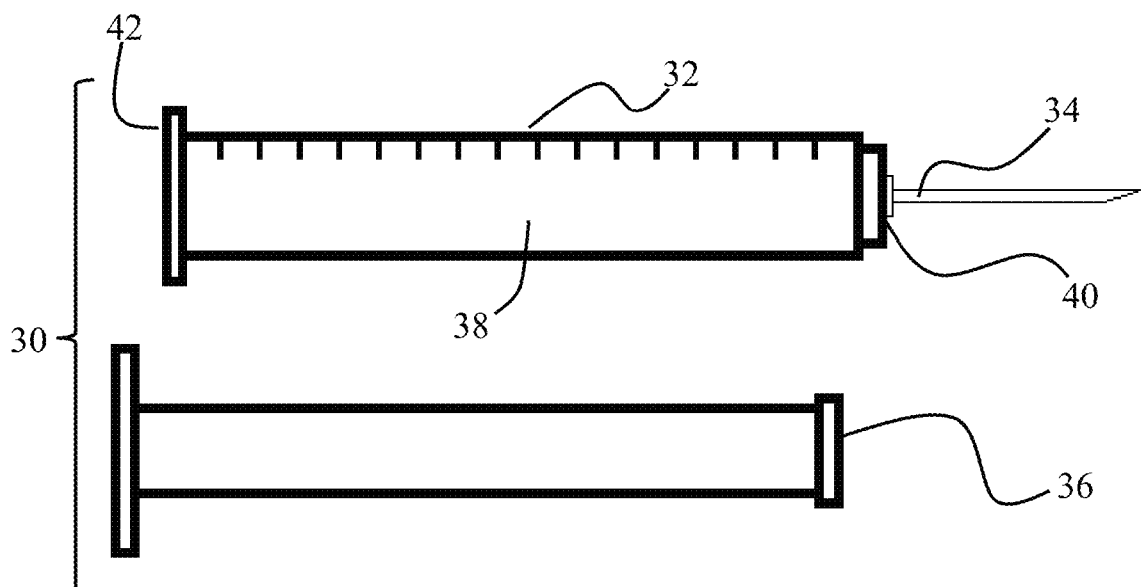
FIG. 3 is a schematic view of a syringe loadable with an anti-coagulant according to certain aspects of the present invention.

Referring now generally to the figures, particularly the lyophilization flow-diagram in FIG. 1 and the spray drying flow-diagram in FIG. 2, methods of preparing a heparin-bulking agent composition, which comprises a heparin component and a bulking agent component, comprise providing a source of heparin having a known activity concentration and a source of at least one bulking agent 10. Both the heparin component and the at least one bulking agent component can be provided as dry components. The heparin component and the at least one bulking agent component can also both be provided in solution. The heparin component can also be provided in solution while the at least one bulking agent component is provided as a dry component, or the heparin component can be provided as a dry component while the at least one bulking agent component is provided in solution.

After the heparin component and the bulking agent component(s) are provided, the heparin component and the bulking agent component(s) are then combined, mixed together, and/or dissolved in solution 12 to provide a heparin-bulking agent formulation. In the situation where either the heparin component, the bulking agent component(s) and/or both the heparin component and the bulking agent component(s) are provided in solution, the solution of the component provided in solution may serve as the solvent to dissolve the heparin and the one or more bulking agents in solution.

In certain aspects, a desired quantity of heparin by weight is determined and measured (by weight or volume) to which a desired amount of at least one bulking agent is determined and measured (by weight or volume) and added before the heparin component and bulking agent component(s) are dissolved in solution 12. In certain aspects, the heparin component may be provided as a raw heparin powder, such as lyophilized heparin, or in solution, and the bulking agent component(s) may be provided as a dry component or in solution, before being combined, mixed together and dissolved 12 in a solvent, such as water. One of ordinary skill in the art will appreciate that the heparin component and the bulking agent component(s), whether as a solution or in dry form, may be combined together in either order. For instance, one or more bulking agent components in dry granular form may be provided into a heparin solution, a raw heparin powder may be provided into a solution of one or more bulking agent components, the heparin and the one or more bulking agent components may be provided in dry form and added to a measured volume of solvent such as water, or the like.

In certain aspects, the at least one bulking agent and heparin are dissolved 12 in solution with the bulking agent component comprising about 60% to about 97% of the heparin-bulking agent mixture by weight of the solid content while the heparin component comprising about 3% to about 40% of the heparin-bulking agent mixture by weight of the solid content, although other ratios greater or less than the foregoing ranges are contemplated herein based upon the respective activity of the heparin component. For example, the bulking agent component may be provided in an amount of about 11 grams while the heparin component is provided in an amount of about 4 grams.

In certain aspects, the method can further comprise an optional solubility step 14, in which a quantity of water (e.g., de-ionized water) is added to the heparin-bulking agent mixture to facilitate the dissolution of the bulking agent and/or heparin into the heparin-bulking agent solution mixture. The amount of water can vary, although in certain aspects the amount of water is added such that there is about 10% to about 25% by weight solid content, and in some other aspects about 10% to about 20% by weight solid content, of the heparin and bulking agent(s) in solution for a subsequent lyophilization process according to the method illustrated in the flow diagram of FIG. 1.

As illustrated in FIG. 1, after the desired heparin-bulking agent formulation in solution is obtained, the method can further comprise a freezing step 16 in which the heparin-bulking agent formulation in solution is cooled to temperatures below about −26° C., in some instances below about −28° C., in some instances below about −30° C., in some instances below about −32° C., and in some other instances below about −35° C. for the mixture to achieve complete solidification. In some aspects, the heparin-bulking agent formulation in solution achieves complete solidification in less than about 1 hour, in some instances less than about 45 minutes, in some instances less than about 30 minutes, in some instances less than about 20 minutes, in some instances less than about 15 minutes, and in some instances less than about 10 minutes. In some instances, the heparin-bulking agent formulation in solution can be frozen to a state of complete solidification at a temperature of about −26° C. to about −80° C. for a freezing period of time of about 10 minutes to about 8 hours.

The method further comprises a primary drying step 18 in which the frozen heparin-bulking agent formulation is lyophilized for a primary period of time. For example, without being bound by limitation, the mixture can be placed within the condenser chamber of a lyophilizer having a temperature of about −50° C. and a system pressure of about 950 mBar absolute for a primary period of about 48 hours. One of ordinary skill in the art will appreciate that other lyophilization temperatures, pressures and periods of time can be utilized and are contemplated herein. For example, in some aspects, the heparin-bulking agent formulation undergoes a lyophilization cycle in which the heparin-bulking agent formulation is exposed to more than one freezing temperature of about −10° C. to about −80° C. for different periods of time, which may also occur under chamber pressure or pressures ranging from about 1 mTorr to about 250 mTorr.

In certain aspects, the solidified heparin-bulking agent formulation is dried to produce a heparing-bulking agent composition having a moisture content less than about 10%, in some aspects less than about 7.5%, in some aspects less than about 5%, in some aspects less than about 2.5%, and in some further aspects less than about 1.5%, during the primary drying step 18.

The method may further comprise a grinding step 20, in which the lyophilized heparin-bulking agent composition is removed from the drying container and ground into a powder. The lyophilized heparin-bulking agent composition can be ground using known milling processes, such as a mortar and pestle, ball mill, hammer mill, cryogenic grinding, cryo-milling, or the like grinding methods for providing a powder with desired particle size so as to allow efficient and accurate powder filling using current powder filling technology.

In certain aspects, the method further comprises an optional second drying step 22 in which the powder is dried for a second period of time. In the optional second drying step 22, the heparin-bulking agent composition can be dried at ambient temperature on a shelf dryer. For instance, without being bound by limitation, the second period of time can comprise about 24 hours, although shorter and longer periods of time are contemplated herein. In one aspect, the moisture content of the heparin-bulking agent composition powder following the second drying step 22 can be less than about 10%, in some aspects less than about 7.5%, in some aspects less than about 5%, in some aspects less than about 2.5%, and in some further aspects less than about 1.5%.

Alternative to the lyophilization process, as shown in the flow diagram of FIG. 2, after the desired heparin-bulking agent formulation in solution is obtained, the method can further comprise spray drying 19 the heparin-bulking agent formulation using a standard spray drying system. For instance, without being bound by limitation, the heparin-bulking agent formulation in solution is spray dried using a spray dryer equipped with a two fluid atomizing nozzle, standard drying chamber, and standard solids separation cyclone.

The method may further comprise a grinding step 20 in which the spray dried heparin-bulking agent mixture is further ground using known milling processes, such as a mortar and pestle, ball mill, hammer mill, cryogenic grinding, cryomilling, or the like grinding methods for providing a powder with desired particle size so as to allow efficient and accurate powder filling using current powder filling technology.

Whether the heparin-bulking agent powder composition is prepared using the lyophilization process illustrated in FIG. 1 or the spray drying process illustrated in FIG. 2, the method can further comprise a filling step 24 in which a container is dry filled with the dried powder using current powder filling technology.

In certain aspects, as shown in FIGS. 3-7, the container in the dry-filling step may be a syringe 30 having a barrel 32, a needle 34 and a plunger 36. The barrel 32 defines an internal volume 38 for receiving the heparin-bulking agent composition 46 in a powder form and a blood sample. The barrel 32 further comprises a first opening 40 at one of the internal volume 38 and a second opening 42 at the opposite end of the internal volume 38. As depicted, the needle 34 is fitted to the first opening 40 and the plunger 36 is insertable into the second opening 42 to draw and expel material through the needle 34 into and out of the internal volume 38. The description of the syringe 30 is not intended to be limiting, but to assist in the description the loading of the syringe 30 with the free-flowing powdered heparin-bulking agent composition.

Figure 4:
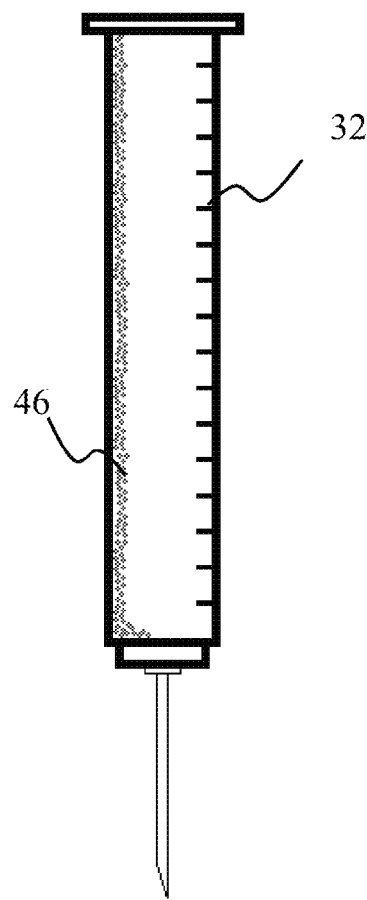
FIG. 4 is schematic view of the syringe depicted in FIG. 3 illustrating filling the syringe with a free-flowing powder of the anti-coagulant.
Figure 5:
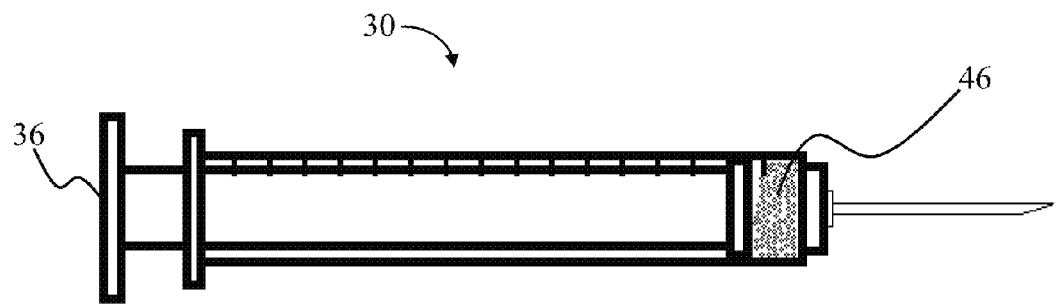
FIG. 5 is schematic view of the syringe depicted in FIG. 3 illustrating the anti-coagulant powder loaded into the syringe and depressed to one end by depressing a plunger.

As shown in FIGS. 4-5, the powdered composition 46 can be dry filled through the second opening 42 into the internal volume 38. The plunger 36 can then be inserted into the second opening 42 and depressed, as shown in FIG. 5, to remove any unused volume within the internal volume 38.

Figure 6:
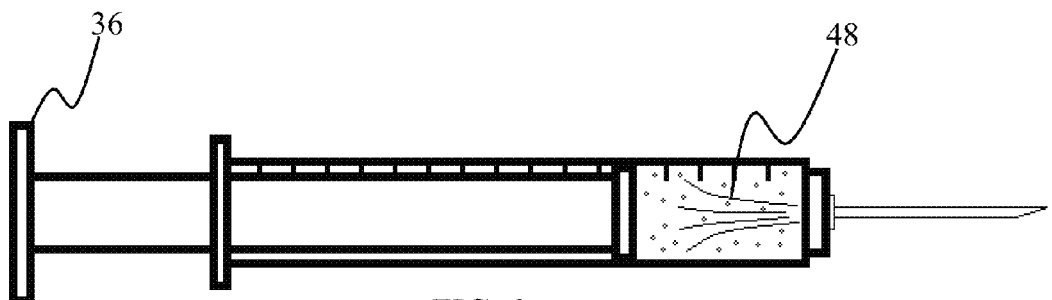
FIG. 6 is a schematic view of the syringe depicted in FIG. 3 illustrating drawing a blood sample into the syringe and dissolving the anti-coagulant powder within the blood sample.
Figure 7:
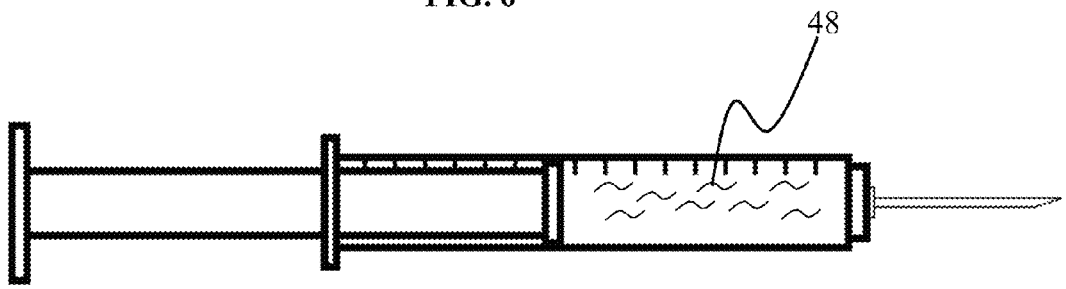
FIG. 7 is a schematic view of the syringe depicted in FIG. 3 loaded with a blood sample containing the dissolved anti-coagulant.

As shown in FIG. 6-7, during use of the syringe 30 containing the powdered heparin-bulking agent composition 46, the plunger 36 can be pulled to create a vacuum within the internal volume 38 and draw a blood sample into the internal volume 38. The flow of the blood sample into the internal volume 38 agitates the powdered heparin-bulking agent composition 46 and dissolves the heparin-bulking agent composition 46 into the blood sample to form a heparin-blood composition 48, the heparin-bulking agent composition 46 used as an anti-coagulant.

Figure 8:
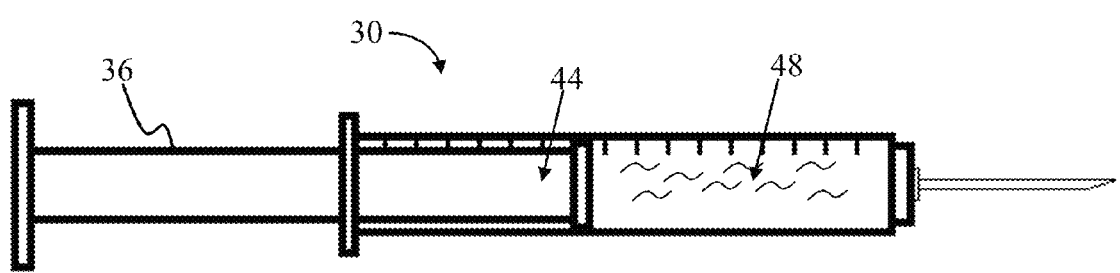
FIG. 8 is a schematic view of a syringe loadable with an anti-coagulant having a preset plunger with a filter tip for arterial blood samples according to certain aspects of the present invention, the arterial blood forcing air past the plunger filter tip until contacting the tip and plugging the filter; the heparin-bulking agent composition of the present invention dissolving as blood fills the syringe barrel.

Referring now to FIG. 8, the syringe 30 containing a free-flowing powder of the heparin-bulking agent composition 48, the plunger 36 can be provided at a preset position and contain a special filter 44 thereon. Thus, when arterial blood is provided into the internal volume 38, wherein the arterial blood forces air past the plunger filter tip 44 until the arterial blood contacts the tip of the plunger thereby plugging the filter 44. The flow of the arterial blood into the internal volume 38 also dissolves the heparin-bulking agent powder composition 46, which serves as an anti-coagulant, to form a heparin-blood composition 48.

As provided by the foregoing syringe embodiments, the powdered heparin-bulking agent composition can be provided in any type of blood sample container where an anti-coagulant is desired, including, but not limited to, such as a blood sample collection tube, a syringe, a vacuum tube, and the like.

In certain aspects, the blood collection container, such as a syringe, contains about 0.5 mg to about 5 mg of the free-flowing, powdered heparin-bulking agent composition, in some other aspects about 1.0 mg to about 3.0 mg, in some other aspects about 1.5 mg to about 2.0 mg, although other amounts greater or less than the foregoing ranges and subranges being contemplated herein. In another aspect, the heparin-bulking agent composition within the respective system has a moisture content less than about 10%, in some aspects less than about 7.5%, in some aspects less than about 5%, in some aspects less than about 2.5%, and in some further aspects less than about 1.5%.

A range of the particle size distribution between the $X_{10}$ and the $X_{90}$ values of the powdered heparin-bulking agent composition may be less than about 320 microns, in some aspects less than about 300 microns, in some aspects less than about 270 microns, and in some other aspects less than about 250 microns. The powdered heparin-bulking agent composition may have a particle size distribution with respect to the $X_{10}$ and the $X_{90}$ values that is in the range between about 4 microns to about 400 microns, in some aspects about 8 microns to about 390 microns, in some aspects about 10 microns to about 380 microns, in some aspects about 15 microns to about 350 microns, in some aspects about 35 microns to about 280 microns, and still in some other aspects about 40 microns to about 380 microns.

In certain aspects of the present invention, the heparin-bulking agent composition in a free-flowing powder has a particle size distribution $X_{10}$ value greater than about 4 microns, in some aspects greater than about 8 microns, in some aspects greater than about 10 microns, in some aspects greater than about 15 microns, in some aspects greater than about 25 microns, and in some aspects greater than about 30 microns. In some aspects, the powdered heparin-bulking agent composition has a particle size distribution $X_{10}$ value in the range of about 4 microns to about 40 microns, in some aspects about 4 microns to about 35 microns, in some aspects about 4 microns to about 30 microns, in some other aspects about 8 microns to about 32 microns, in some aspects about 8 microns to about 18 microns, in some aspects about 10 microns to about 18 microns, and in some other aspects about 25 microns to about 40 microns.

In certain aspects of the present invention, the powdered heparin-bulking agent has a particle size distribution $X_{90}$ value less than about 400 microns, in some aspects less than about 390 microns, in some aspects less than about 350 microns, in some aspects less than about 340 microns, in some aspects less than about 320 microns, in some aspects less than about 300 microns, in some aspects less than about 280 microns, and in some other aspects less than about 260 microns. In some aspects, the powdered heparin-bulking agent composition has a particle size distribution $X_{90}$ value in the range of about 260 microns to about 400 microns, in some aspects about 260 microns to about 280 microns, in some aspects about 280 microns to about 400 microns, in some other aspects about 280 microns to about 320 microns, in some aspects about 280 microns to about 340 microns, in some aspects about 250 microns to about 320 microns, and in some other aspects about 300 microns to about 320 microns.

In certain aspects of the present invention, the powdered heparin-bulking agent composition has a particle size distribution $X_{50}$ value in the range of about 80 microns to about 140 microns, in some aspects about 80 microns to about 100 microns, in some aspects about 85 microns to about 95 microns, in some aspects about 120 microns to about 140 microns, and in some other aspects about 125 microns to about 135 microns.

With respect to a syringe loaded with a heparin-bulking agent composition of the present invention, at least a portion of the barrel of the syringe is pre-loaded with the free-flowing powdered anti-coagulant, the syringe having a plunger and a needle. The plunger of the syringe is pulled to create a vacuum within the barrel to pull a blood sample into the barrel, wherein the flow of blood into the barrel circulates and dissolves the anti-coagulant into the blood. Alternatively, arterial blood may be allowed to fill a syringe pre-loaded with the free-flowing powdered anti-coagulant, the syringe having a pre-set plunger position, wherein the flow of blood into the barrel circulates and dissolves the anti-coagulant into the blood. The syringe, or an aliquot of the blood sample having the dissolved anti-coagulant from the syringe, may be placed into a blood analyzer for analysis. Alternatively, the plunger can be actuated to expel the blood sample and anti-coagulant mixture into a sample blank that is insertable into a blood analyzer for analysis.

WORKING EXAMPLES

Example 1

The effect of lyophilization on the heparin-bulking agent formulation was tested by combining 60 ml of heparin solution containing about 2556 mg of heparin with about 7274 mg of bulking agent, wherein the bulking agent was sucrose, mannitol, trehalose or raffinose. 60 ml of de-ionized water was added to the heparin-bulking agent mixture to fully dissolve the bulking agent. The heparin-bulking agent mixture was then lyophilized for about 48 hours at about −50° C. in a lyophilizer having a system pressure of about 950 mBar absolute. The lyophilized heparin-bulking agent composition was then ground into a powder before being dried at ambient temperature for about 24 hours. The resulting heparin-bulking agent compositions in a dried powder form were evaluated for yield (weight), residual moisture and flow-ability characteristics.

| Bulking Agent | Yield (g) | [WT] % Residual Moisture |
|---|---|---|
| Sucrose | 9.21 | Not Determined |
| Mannitol | 9.31 | 2.7% |
| Trehalose | 7.57 | 3.3% |
| Raffinose | 7.88 | 3.3% |

All four formulations dried easily with mannitol having the best appearing cake and lowest bulk density, trehalos and raffinose having the freest flowing powder, and sucrose producing a slightly glassy cake after drying.

Example 2

The effect of spray drying on the heparin-bulking agent formulation was tested by combining 200 ml of heparin solution containing about 8520 mg of heparin with about 24240 mg of bulking agent and mixed until the bulking agent is dissolved into the heparin solution. The bulking agent was selected from sucrose, trehalose, raffinose and mannitol. The heparin-bulking agent mixture was then successfully spray dried at different sprayer inlet temperatures ranging from about 115° C. to about 175° C., sprayer outlet temperatures ranging from about 50° C. to about 65° C., heparin-bulking agent mixture feed rates of about 6 ml/min to about 9 ml/min, while obtaining the following residual moisture of the dried heparin-bulking agent mixture.

| Bulking Agent | [WT] % Residual Moisture Spray dried |
|---|---|
| Mannitol | 3.9% |
| Trehalose | 8.2% |
| Raffinose | 7.7% |

These results demonstrate that the heparin-bulking agent composition can be spray dried and were not optimized for a final low or otherwise desired residual moisture content. In certain aspects, the final particulate size of the dried heparin-bulking agent formulation can be controlled by adjusting the droplet size exiting the sprayer nozzle. The droplet size can be adjusted such that milling of the dried heparin formulation to the desired particulate size for the powder is not necessary or otherwise an optional step. In certain aspects, the final particulate size can be controlled by altering the milling speed and passing the milled particulates through a sieve screen. In certain aspects, the dried heparin formulation can be milled at 2000 RPM and passed through a 0.050 mm screen to provide a consistent particulate size without clumping.

Example 3

1.5 mg of the powdered heparin-bulking agent mixtures with different bulking agents were loaded into a syringe 30 for evaluating the differences between the flowability and dissolution characteristics when the powder is formed by lyophilization or spray dried. A surrogate blood buffer solution was introduced into the syringe at a rate approximating the flow rate of blood collected from an artery.

| Bulking Agent | Drying Method | Dry Filing Characteristics | Dissolution Characteristics |
|---|---|---|---|
| Mannitol | Lyophilized | Acceptable fill characteristics | The formulation can initially form clumps that dissolve with minor agitation |
| Mannitol | Spray Dried | Acceptable fill characteristics (product light dusting, light static) | Small amounts of floating clumps of the formulation can form |
| Raffinose | Lyophilized | Acceptable fill characteristics | The formulation dissolves with minor agitation |
| Raffinose | Spray Dried | Acceptable fill characteristics | Large amounts of floating clumps of the formulation can form |
| Trehalose | Lyophilized | Acceptable fill characteristics | Small amounts of floating clumps of the formulation can form |
| Trehalose | Spray Dried | Acceptable fill characteristics (product can clump into semi-solid slug formations) | The formulation easily dissolves |

The heparin-bulking agent powdered compositions using raffinose and trehalose as the bulking agent were further evaluated for shelf-life using an accelerated shelf-life protocol to simulate real time shelf life. To conduct the accelerated shelf-life analysis, the stability of the powdered samples was determined using Anti-Factor IIa test methodology following the USP Monograph with guidance for using elevated temperature to simulate real time following ASTM F1980 standard testing at a conditioning temperature of 50° C. Material from pre-gamma, T=0 equivalent year, T=1 equivalent year, T=3 equivalent year and T=5 equivalent year were analyzed for anti-Factor IIa testing, which as shown in the following tables show no real trending.

|           | Trehalose - Lyophilized Anti-Factor IIa (units/mg) | Trehalose - Spray Dried Anti-Factor IIa (units/mg) |
|-----------|---------------------------------------------------|----------------------------------------------------|
| Pre-gamma | 45                                                | 44.1                                               |
| T = 0     | 45                                                | 46.4                                               |
| T = 1     | 38.8                                              | 44.6                                               |
| T = 3     | 43.1                                              | 39.4                                               |
| T = 5     | 42.4                                              | 40.7                                               |

|           | Raffinose - Lyophilized Anti-Factor IIa (units/mg) | Raffinose - Spray Dried Anti-Factor IIa (units/mg) |
|-----------|---------------------------------------------------|----------------------------------------------------|
| Pre-gamma | 44.6                                              | 53.4                                               |
| T = 0     | 43.5                                              | 42.4                                               |
| T = 1     | 46                                                | 44.8                                               |
| T = 3     | 44.1                                              | 38.5                                               |
| T = 5     | 46.7                                              | 45.9                                               |

Example 4

In the following example, a first heparin-bulking agent composition contains D-mannitol as the bulking agent (referred to in this example for ease of reference as "heparin-mannitol composition"), and a second heparin-bulking agent composition contains α,α-Trehalose as the bulking agent (referred to in this example for ease of reference as "heparin-trehalose composition").

With respect to the preparation of the heparin-mannitol composition, 61.5 grams of a lyophilized lithium salt of heparin and 163.5 grams of D-mannitol were combined together, to which 1000 mL of purified water and 6.14 grams of a calcium acetate stock solution (the calcium acetate stock solution comprising 0.100 grams of calcium acetate dissolved in 100 ml of purified water) were added. The calcium acetate is added to the formulation to negate any effect the heparin activity may have on the calcium analysis of a blood sample, including artificially low calcium values. The combined components were stirred until dissolved in solution and then the solution was brought to volume by adding purified water to equal 1500 ml of a prepared heparin-mannitol formulation.

With respect to the preparation of the heparin-trehalose composition, 61.51 grams of lyophilized lithium salt of heparin and 180.59 grams of α,α-Trehalose were combined, to which 1000 mL of purified water and 6.15 grams of the calcium acetate stock solution were added. The combined components were stirred until dissolved in solution and then the solution was brought to volume by adding purified water to equal 1500 ml of a prepared heparin-trehalose formulation.

Once the heparin-bulking agent formulations were prepared, the respective heparin-bulking agent formulations underwent a lyophilization cycle process, which includes pre-chilling the lyophilizer to 4° C. at an ambient temperature, adding 1500 mL of the respective heparin-bulking agent formulation into a disposable lyophilization tray and placed into the pre-chilled lyophilizer, and then running a programmed lyophilization cycle on the heparin-bulking agent formulation that includes ramp and hold steps at various pressures, temperatures and periods of time. In particular, the heparin-mannitol formulation underwent a lyophilization cycle process provided in Table 6.

TABLE 6

Lyophilization Cycle Process of Heparin-Mannitol Formulation

| | | | Temperature (° C.) | | | Pressure (mTorr) | |
|---|---|---|---|---|---|---|---|
| | | Time | Shelf | Product - | Product - | | |
| Step | Process | (hr) | Set | Start | End | Start | Beginning | End |
| 1 | Load | 0.5 | +4.0 | — | +3.5 | Ambient | Ambient | Ambient |
| 2 | Ramp | 1.0 | −40 | +3.5 | −42.1 | Ambient | Ambient | Ambient |
| 3 | Hold | 1.0 | −40 | −42.1 | −42.1 | 200 | Ambient | 183 |
| 4 | Ramp | 1.0 | −10 | −42.1 | −36.5 | 200 | 183 | 188 |
| 5 | Hold | 15 | −10 | −36.5 | −35.3 | 200 | 188 | 188 |
| 6 | Hold | 15 | −10 | −35.3 | −19.9 | 100 | 188 | 90 |
| 7 | Ramp | 2.0 | +25 | −19.9 | −0.8 | 0 | 90 | 97 |
| 8 | Hold | 4.5 | +25 | −0.8 | +15.2 | 0 | 97 | 14 |
| Cycle time | | 40 | | | | | | |

Similarly, the heparin-trehalose formulation underwent a lyophilization cycle process provided in Table 7.

TABLE 7

Lyophilization Cycle Process of Heparin-Trehalose Formulation

| | | | Temperature (° C.) | | | Pressure (mTorr) | |
|---|---|---|---|---|---|---|---|
| | | Time | Shelf | Product - | Product - | | |
| Step | Process | (hr) | Set | Start | End | Start | Beginning | End |
| 1 | Load | 0.5 | +4.0 | — | +3.9 | Ambient | Ambient | Ambient |
| 2 | Ramp | 1.0 | −40 | +3.9 | −30.1 | Ambient | Ambient | Ambient |

TABLE 7-continued

Lyophilization Cycle Process of Heparin-Trehalose Formulation

| | | | Temperature (° C.) | | | | |
| | | | Shelf | Product - | Product - | Pressure (mTorr) | | |
| Step | Process | Time (hr) | Set | Start | End | Start | Beginning | End |
| --- | --- | --- | --- | --- | --- | --- | --- | --- |
| 3 | Hold | 0.5 | −40 | −30.1 | −38.1 | 200 | Ambient | 184 |
| 4 | Ramp | 1.0 | −10 | −38.1 | −31.1 | 200 | 184 | 184 |
| 5 | Hold | 18 | −10 | −31.1 | −14.5 | 200 | 184 | 185 |
| 6 | Ramp | 2.0 | +25 | −14.5 | ~+10 | 0 | 185 | 193 |
| 7 | Hold | 6 | +25 | ~+10 | +10.6 | 0 | 193 | 17 |
| Cycle time | | 31.5 | | | | | | |

With respect to the heparin-mannitol composition, the phase transition temperature acquired from a resistance graph suggests that cooling to below temperatures of at least −23° C. would be required for achieving solidification during freezing. Observations under the microscope suggest cooling to below temperatures of at least −18° C. would be required for achieving solidification. Since, visual observations under the freeze drying microscope are more accurate, it is recommended that the material be cooled to temperatures below −18° C. to achieve complete solidification.

The electrical resistance graph notes changes at −23° C. during warming. LT-DSC indicated that a glass transition occurred at −32° C. Observations under the microscope revealed the formation of voids at temperatures as low as −30° C. Also, darkened bands, followed by glistening, were observed along the top edge of the sample at temperatures of −49° C. However, it appeared that these darkened areas and glistening did not affect nor prevent continued drying of the sample. Thus, product temperatures should be maintained at or below a range of −32° C. to −34° C. for complete drying with retention of the structure established during the freeze and the absence of collapse.

With respect to the heparin-trehalose composition, the phase transition temperature acquired from a resistance graph suggests that cooling to below temperatures of at least −26° C. would be required for achieving solidification during freezing. Observations under the microscope also suggest cooling to below temperatures of at least −26° C. would be required for achieving solidification. Therefore, it is recommended that the material be cooled to temperatures below −26° C. to achieve complete solidification.

The electrical resistance graph notes changes at −26° C. during warming. LT-DSC indicated a glass transition occurred at −32° C. Observations under the microscope revealed void formation beginning at temperatures as low as −31° C. Also, areas of darkened material were observed along the top edge of the sample at temperatures of −49° C. In addition, small glistening areas were observed near the darkened material at temperatures of −43° C. However, it appeared that these darkened areas and glistening did not affect nor prevent continued drying of the sample. Thus, product temperatures should be maintained at or below a range of −33° C. to −35° C. for complete drying with retention of the structure established during the freeze and the absence of collapse.

After lyophilizing the heparin-bulking agent formulations to form the respective heparin-mannitol composition and heparin-trehalose composition, the lyophilization trays were removed from the lyophilizer, the solid cake was removed and weighed. The lyophilized heparin-mannitol composition weighed 230.97 grams, which resulted in a yield from the 1500 ml of about 15.40%. The lyophilized heparin-trehalose composition weighed 231.04 grams, which resulted in a yield from the 1500 ml of about 15.40%.

The lyophilized heparin-bulking agent compositions were then ground using hammer mill processing. It was determined that hammer mill processing utilizing a 0.050" screen at speed of about 2000 rpm for about 2 to about 3 minutes provided free-flowing powder granules having a consistent particle size for both compositions. The heparin-mannitol composition after milling weighed 195.36 grams, which resulted in a yield after milling of about 13.02%. The heparin-trehalose composition after milling weighed 204.81 grams, which resulted in a yield after milling of about 13.65%.

Both the heparin-mannitol and the heparin-trehalose compositions underwent moisture content analysis using the Karl Fischer process. The average moisture content of two samples of the free-flowing, powdered heparin-mannitol composition was about 5.2%, while the average moisture content of three samples of the free-flowing, powdered heparin-trehalose composition was about 6.3%.

Figure 11:
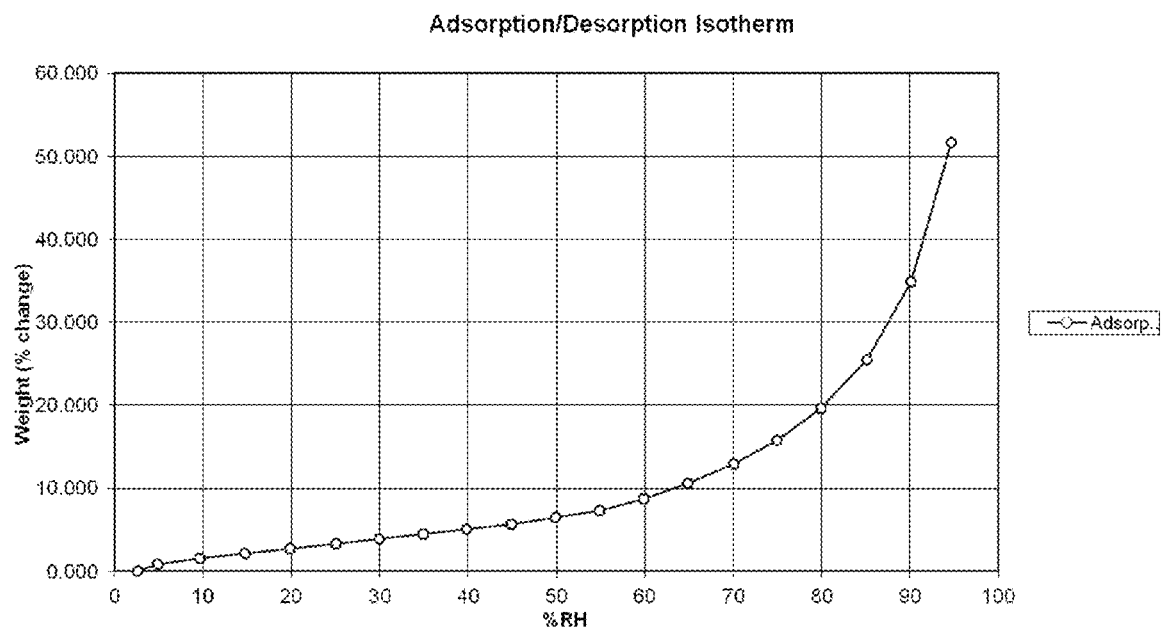
FIG. 11 is a water adsorption/desorption isotherm graph of a free-flowing powder of a heparin-bulking agent composition of the present invention after a milling process, the bulking agent being mannitol.
Figure 12:
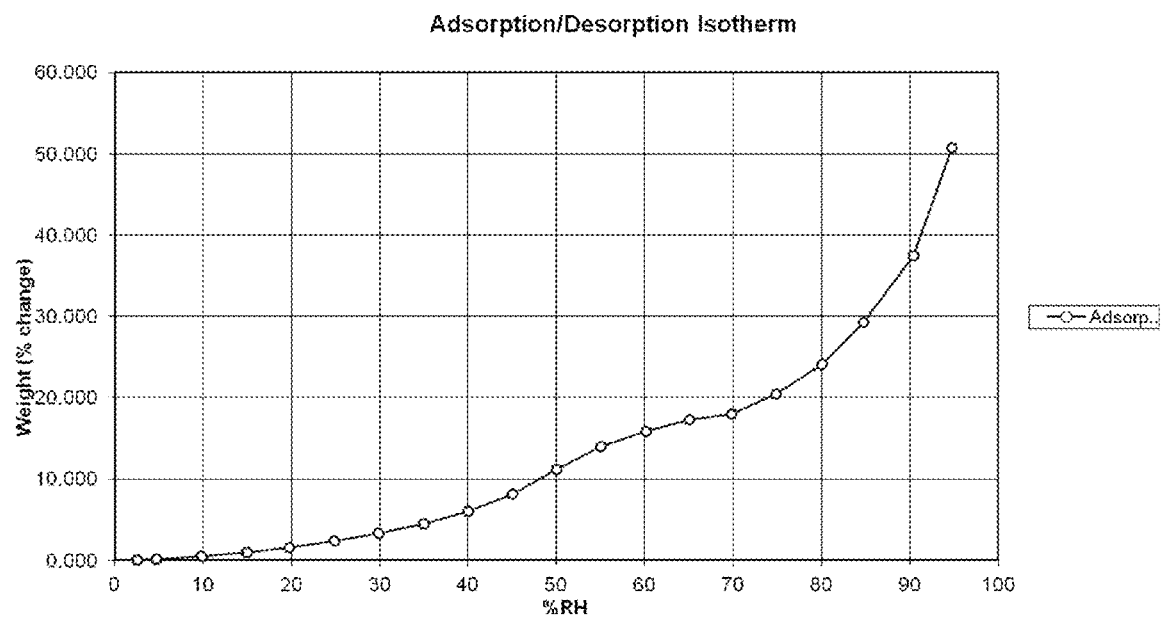
FIG. 12 is a water adsorption/desorption isotherm graph of a free-flowing powder of a heparin-bulking agent composition of the present invention after a milling process, the bulking agent being trehalose.

Samples of the heparin-mannitol composition and heparin-trehalose composition were also placed on a microbalance to determine the weight gain of the samples at a percentage of relative humidity. The resulting adsorption/desorption isotherm graphs of the heparin-mannitol composition is shown in FIG. 11 and that of the heparin-trehalose composition is shown in FIG. 12. These isotherms illustrate that the heparin-trehalose composition has a greater rate of adsorption than the heparin-mannitol composition, with both heparin-bulking agent compositions having about 50% weight change at about 95% relative humidity.

Both the heparin-mannitol composition and the heparin-trehalose composition were tested for dissolution time as pre-sterile material and post-sterile material in both gamma and electron beam (E-beam) methods at 40 kGy. A laboratory device that simulates the force of arterial blood entering a syringe was used with Hanks Buffer as the liquid. The heparin-bulking agent formulations were frozen on the lyophilizer shelf. The dissolution results are summarized in Table 8.

The results as provided in Table 8 illustrate that the pre-lyophilization freezing yielded an acceptable dissolution characteristic for the heparin-trehalose composition, but not for the heparin-mannitol composition. As a result, a second pre-lyophilization freezing method was tested for the heparin-mannitol formulation, which included freezing the liquid solution of the heparin-mannitol formulation on dry ice in an insulated chamber. It was observed that the rate of freezing was much quicker than freezing the formulation on the lyophilizer shelf. An X-ray powder diffraction and crystallinity of the heparin-mannitol compositions (lyophilizer shelf freezing and dry ice freezing) resulted in the heparin-mannitol composition frozen by the dry ice method with a greater percentage of crystallinity. In some instances the pre-lyophilization freezing temperature is at least −70° C. In particular, the heparin-mannitol composition prepared by freezing the formulation on the lyophilizer shelf resulted in about 70% crystalline to 29% amorphous, while the heparin-mannitol composition prepared by freezing the heparin-mannitol composition using dry ice resulted in about 78% crystalline to 22% amorphous. The subsequent dissolution test yielded an instantaneous dissolution of the heparin-mannitol composition that underwent a lower temperature of pre-lyophilization solidification using dry ice.

TABLE 8

Dissolution Testing Results.

| | Lyophilized Heparin with Mannitol Bulking Agent Dissolution time (s) | Lyophilized Heparin with Trehalose Bulking Agent Dissolution time (s) | Pre-Lyophilization Freezing (Heparin- Mannitol Bulking Agent) Dissolution time (s) |
|---|---|---|---|
| Pre-sterile | 39 | 6.5 | Instantaneous (<1) |
| Gamma | >60 (or did not dissolve) | 3.2 | Instantaneous (<1) |
| E-beam | >40 | 5.2 | Instantaneous (<1) |

The stability of the heparin activity post-sterilization was also analyzed for the heparin-bulking agent compositions. In this analysis, both compositions were subjected to 40 kGy using both gamma and E-beam methods. Accelerated shelf life following ASTM F1980 at a conditioning temperature of 55° C., which uses the Q10=2 (which means that for every 10° C. rise in temperature, the rate of chemical reactions generally doubles) was conducted for a simulated four years. There was no statistical difference between pre-sterile and post sterile using both gamma and E-beam. Results provided in Table 9 (heparin-mannitol composition) and Table 10 (heparin-trehalose composition) are reported in International Units of heparin/mg using the Anti-factor IIa assay method.

TABLE 9

Stability of Heparin Activity Post-Sterilization: Heparin-Mannitol Composition
Lyophilized Heparin with Mannitol Bulking Agent

| | Electron Beam | | | Gamma | | |
|---|---|---|---|---|---|---|
| | Test 1 | Test 2 | Avg. | Test 1 | Test 2 | Avg. |
| Pre-sterile | 41.8 | 41.3 | 41.6 | 41.8 | 41.3 | 41.6 |
| T = 0 | 39.3 | 39.8 | 39.6 | 41.9 | 41.1 | 41.5 |
| T = 1 | 40.9 | 40.6 | 40.8 | 41.1 | 40.9 | 41.0 |
| T = 2 | 39.6 | 39.4 | 39.5 | 41.1 | 41.2 | 41.2 |
| T = 3 | 41.6 | 41.8 | 41.7 | 41.4 | 41.6 | 41.5 |
| T = 4 | 41.0 | 42.0 | 41.5 | 41.1 | 41.1 | 41.1 |

TABLE 10

Stability of Heparin Activity Post-Sterilization: Heparin-Trehalose Composition
Lyophilized Heparin with Trehalose Bulking Agent

| | Electron Beam | | | Gamma | | |
|---|---|---|---|---|---|---|
| | Test 1 | Test 2 | Avg. | Test 1 | Test 2 | Avg. |
| Pre-sterile | 41.4 | 41.1 | 41.3 | 41.4 | 41.1 | 41.3 |
| T = 0 | 42.1 | 41.4 | 41.8 | 39.2 | 41.4 | 40.3 |
| T = 1 | 42.2 | 41.6 | 41.9 | 41.8 | 41.6 | 41.7 |
| T = 2 | 41.4 | 41.2 | 41.3 | 43.4 | 43.0 | 43.2 |

TABLE 10-continued

Stability of Heparin Activity Post-Sterilization: Heparin-Trehalose Composition
Lyophilized Heparin with Trehalose Bulking Agent

| | Electron Beam | | | Gamma | | |
|---|---|---|---|---|---|---|
| | Test 1 | Test 2 | Avg. | Test 1 | Test 2 | Avg. |
| T = 3 | 41.2 | 41.7 | 41.5 | 40.9 | 41.4 | 41.2 |
| T = 4 | 42.0 | 41.9 | 41.9 | 41.8 | 42.2 | 42.0 |

These results demonstrate that there is no significant change in the reactivity of the anti-coagulants having either a mannitol bulking agent or a trehalose bulking agent over the simulated time period of 4 years.

The particle size distributions of the powdered heparin-mannitol composition and the powdered heparin-trehalose composition were also determined, the particle size distribution values summarized in Table 11.

TABLE 11

Particle Size Distribution

| | $X_{10}$ (microns) | $X_{50}$ (microns) | $X_{90}$ (microns) |
|---|---|---|---|
| Heparin-Mannitol Samples | — | — | — |
| T = 0 Gamma | 9.62 | 91.58 | 276.82 |
| T = 0 E-beam | 10.79 | 97.99 | 279.11 |
| Pre-Sterile | 16.58 | 104.74 | 279.11 |
| Heparin-Trehalose Samples | — | — | — |
| T = 0 Gamma | 31.40 | 129.61 | 318.92 |
| T = 0 E-beam | 39.24 | 156.26 | 388.83 |
| Pre-Sterile | 33.57 | 123.44 | 281.94 |

Figure 9:
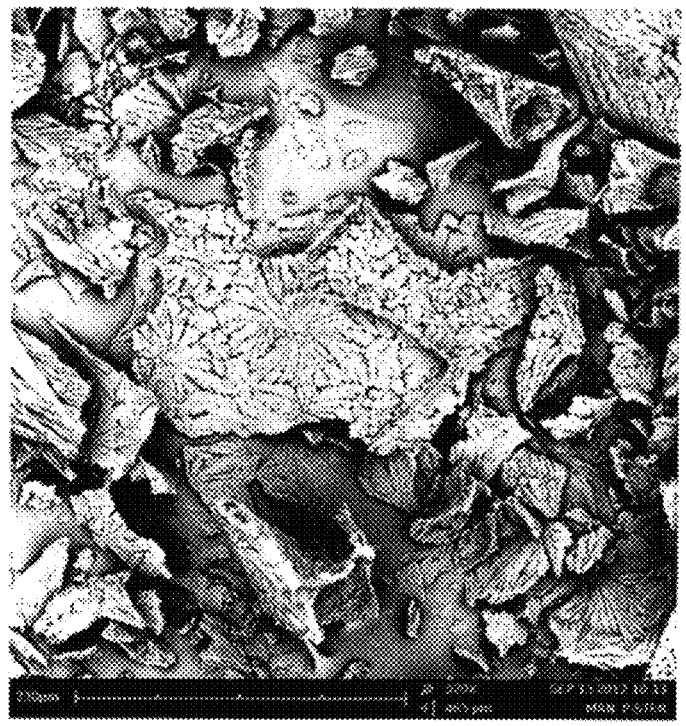
FIG. 9 is an SEM image of a free-flowing powder of a heparin-bulking agent composition of the present invention after a milling process, the bulking agent being mannitol.
Figure 10:
FIG. 10 is an SEM image of a free-flowing powder of a heparin-bulking agent composition of the present invention after a milling process, the bulking agent being trehalose.

As provided by the data in Table 8, the heparin-mannitol composition was capable of being ground such that at least 90% of the particulates were less than about 280 microns, the median value was about 90 microns to about 105 microns, and at least 10% of the particulates were less than about 20 μm. Similarly, the heparin-trehalose composition was capable of being ground such that at least 90% of the particulates were less than about 390 microns, the median value was about 120 microns to about 160 microns, and at least 10% of the particulates were less than about 40 μm. Further, the range between the $X_{10}$ and the $X_{90}$ values was relatively narrow being less than about 270 microns for the heparin-mannitol composition and less than about 350 microns for the heparin-trehalose composition. One of ordinary skill in the art will appreciate that the heparin-bulking agent compositions can be ground using various different grinding processes with desired particle sizes and/or particle size ranges being achieved. FIG. 9 is an SEM image at 520× of a sample of the powdered heparin-mannitol composition after the milling process to form a free-flowing powder, with the bar scale being 230 microns. FIG. 10 is an SEM image at 475× of a sample of the heparin-trehalose composition after the milling process to form a free-flowing powder, with the bar scale being 250 microns.

The bulk density and the tapped density of the powdered heparin-mannitol composition and the powdered heparin-trehalose composition were also determined, the bulk density being the powder in the virgin state as poured while the tapped density measuring the density of the powder after 500 and 750 drops or taps to determine the settling and packing characteristics. The tapped density is a simulation of the change in density of the powdered anti-coagulant compositions from normal movement and settling. The bulk density and tapped density of the heparin-bulking agent compositions are summarized in Table 12.

TABLE 12

Bulk Density and Tapped Density

| | Lyophilized Heparin with Mannitol Bulking Agent Density (gm/cc) | Lyophilized Heparin with Trehalose Bulking Agent Density (gm/cc) |
|---|---|---|
| Initial density | 0.221 | 0.429 |
| After 500 taps | 0.276 | 0.573 |
| After 750 taps | 0.276 | 0.614 |

These results demonstrate that the powdered heparin-mannitol composition only had a 20% change in density from the bulk density to the tapped density after 500 taps. The powdered heparin-trehalose composition is almost twice as dense as the powdered heparin-mannitol composition, and the powdered heparin-trehalose composition continued to pack even after 750 taps.

The fillability of the powdered heparin-mannitol composition and heparin-trehalose composition were also tested using a hand volumetric powder filler manufactured by M&) Perry in Corona, Calif. Both the powdered heparin-mannitol composition and the heparin-trehalose composition were free-flowing such that the powders filled easily and accurately. The fillability of the powdered heparin-trehalose composition was most effective at environments having less than about 5% relative humidity, where the composition absorbed minimal amounts of moisture.

While the invention is amenable to various modifications and alternative forms, specifics thereof have been shown by way of example in the drawings and described in detail. It is understood, however, that the intention is not to limit the invention to the particular embodiments described. On the contrary, the intention is to cover all modifications, equivalents, and alternatives falling within the spirit and scope of the invention as defined by the appended claims.

The invention claimed is:

1. A method of preparing a heparin-bulking agent composition, the method comprising:
    providing a heparin component and at least one bulking agent;
    dissolving the heparin component and the at least one bulking agent in a solution to form a heparin-bulking agent formulation;
    drying the heparin-bulking agent formulation to form a heparin-bulking agent composition having a solid mass, the heparin component comprising about 3% to about 40% by weight of the solid mass and intermixed with the bulking agent comprising about 60% to about 97% by weight of the solid mass; and
    grinding the solid mass of the heparin-bulking agent composition to a particulate size having an $X_{10}$ and $X_{90}$ value particle size distribution range between about 35 microns and about 400 microns such that the heparin-bulking agent composition comprises a free-flowing powder that is readily dissolvable upon contact with a blood sample in under 10 seconds.

2. The method of claim 1, wherein the heparin component is a heparin salt chosen from lithium, sodium, calcium, zinc or combinations thereof.

3. The method of claim 2, wherein the heparin component is provided as a solution, an aqueous solution, a solid material, or a lyophilized heparin salt.

4. The method of claim 2, wherein the bulking agent is a water soluble material chosen from a sugar alcohol, a carbohydrate, a water-soluble polymer, or combinations thereof.

5. The method of claim 4, wherein the water soluble material is selected from the group consisting of mannitol, trehalose, raffinose, sorbitol, sucrose, lactose, polyvinylpyrrolidone, and combinations thereof.

6. The method of claim 5, wherein the water soluble bulking agent is provided as an aqueous solution or a solid material.

7. The method of claim 4, further comprising mixing the heparin component and the bulking agent component in an aqueous solution until dissolved to form the heparin-bulking agent formulation.

8. The method of claim 4, wherein the heparin-bulking agent formulation is lyophilized to form the heparin-bulking agent composition.

9. The method of claim 8, further comprising freezing the heparin-bulking agent formulation to form a solidified heparin-bulking agent formulation prior to lyophilizing the heparin-bulking agent formulation.

10. The method of claim 9, wherein the solidified heparin-bulking agent formulation is lyophilized at a temperature below about −32° C.

11. The method of claim 4, wherein the heparin-bulking agent formulation is spray dried to form the heparin-bulking agent composition.

12. The method of claim 1, wherein the heparin-bulking agent formulation is spray dried to form the heparin-bulking agent composition.

13. The method of claim 12, wherein a sprayer inlet temperature is in the range of about 115° C. to about 175° C. and a sprayer outlet temperature is in the range of about 50° C. to about 65° C.

14. The method of claim 1, wherein a moisture content of the heparin bulking agent composition is less than about 10%.

15. The method of claim 1, wherein a sterilization stability of the free-flowing powder of the heparin-bulking agent composition is substantially unchanged over a period of about 5 years.

16. The method of claim 1 further comprising filling a blood collection container with a predetermined amount of the free-flowing powder of said heparin-bulking agent composition.

17. An anti-coagulant comprising:
    a plurality of particles of a heparin-bulking agent composition, each of the plurality of particles of the heparin-bulking agent composition having a heparin component intermixed with a bulking agent component, wherein the plurality of particles of the heparin-bulking agent composition are ground into a free-flowing powder adapted for use with a powder filling apparatus; wherein the plurality of particles of the heparin-bulking agent composition have an $X_{10}$ and $X_{90}$ value particle size distribution range between about 35 microns and about 400 microns;
    wherein a predetermined amount of the free-flowing powder is readily dissolvable within a blood sample in under 10 seconds; and
    wherein the heparin component comprises about 3% to about 40% by weight of a solid content of each of the plurality of particles of the heparin-bulking agent composition and the bulking agent comprises about 60% to about 97% by weight of the solid content of each of the plurality of particles of the heparin-bulking agent composition.

18. The anti-coagulant of claim 17, wherein the heparin component is a heparin salt selected from the group consisting of lithium, sodium, calcium, zinc and combinations thereof.

19. The anti-coagulant of claim 18, wherein the bulking agent is a water soluble material selected from the group consisting of a sugar alcohol, a carbohydrate, a water-soluble polymer, and combinations thereof.

20. The anti-coagulant of claim 19, wherein the water soluble material is selected from the group consisting of mannitol, trehalose, raffinose, sorbitol, sucrose, lactose, polyvinylpyrollidone, and combinations thereof.

21. The anti-coagulant of claim 17, wherein the range of particle size distribution between the $X_{10}$ and $X_{90}$ value for each of the plurality of particles of the heparin-bulking agent composition is between about 40 microns and about 380 microns.

22. The anti-coagulant of claim 17, wherein a moisture content of the heparin-bulking agent composition is less than about 10%.

23. The anti-coagulant of claim 18, wherein the heparin-bulking agent composition is a lyophilized heparin-bulking agent composition or a spray dried heparin-bulking agent composition.

24. The anti-coagulant of claim 18, wherein said anti-coagulant is pre-loaded into a blood collection container.

25. A blood collection container comprising the anti-coagulant as set forth in claim 18 pre-loaded into said container, wherein the anti-coagulant has a dissolution of less than about 10 seconds upon a blood sample being added to the blood collection container.

26. A blood collection container comprising the anti-coagulant as set forth in claim 18 pre-loaded into said container, wherein the anti-coagulant has a dissolution of less than about 10 seconds upon a blood sample being added to the blood collection container without the need of agitating the blood collection container to dissolve the anti-coagulant within the blood sample.

27. A blood collection device, comprising:
a container having an internal volume capable of receiving a blood sample; and
a predetermined amount of a free-flowing powder of an anti-coagulant loaded into the internal volume of the container, the anti-coagulant comprising a heparin-bulking agent composition, the heparin-bulking agent composition having a heparin component intermixed with a bulking agent component, wherein the free-flowing powder comprises a plurality of particles having an $X_{10}$ and $X_{90}$ value particle size distribution range between about 35 microns and about 400 microns, wherein the predetermined amount of the free-flowing powder is readily dissolvable within a blood sample in under 10 seconds, and wherein the heparin component comprises about 3% to about 40% by weight of a solid content of each of the plurality of particles of the heparin-bulking agent composition and the bulking agent comprises about 60% to about 97% by weight of the solid content of each of the plurality of particles of the heparin-bulking agent composition.

28. The blood collection device of claim 27, wherein the heparin-bulking agent composition is dissolvable within the blood sample received within the internal volume.

29. The blood collection device of claim 27, wherein the heparin component is a heparin salt chosen from lithium, sodium, calcium, zinc or combinations thereof.

30. The blood collection device of claim 27, wherein the bulking agent is a water soluble material chosen from a sugar alcohol, a carbohydrate, a water-soluble polymer, or combinations thereof.

31. The blood collection device of claim 30, wherein the water soluble material is selected from the group consisting of mannitol, trehalose, raffinose, sorbitol, sucrose, lactose, polyvinylpyrrolidone, and combinations thereof.

32. The blood collection device of claim 27, wherein a moisture content of the heparin-bulking agent composition is less than about 10%.

33. The blood collection device of claim 27, wherein the container is a blood sample collection tube, a syringe, or a vacuum tube.

34. The blood collection device of claim 27, wherein internal volume of the container between about 0.5 mg to about 5.0 mg of the heparin-bulking agent composition.

35. The blood collection device of claim 27, wherein the anti-coagulant is capable of being dissolved within a blood sample of a patient in less than about 10 seconds upon the blood sample being added to the internal volume of the blood collection container without the need of agitating the blood collection container to dissolve the anti-coagulant within the blood sample.

36. The blood collection device of claim 27, wherein a sterilization stability of the free-flowing powder of the heparin-bulking agent composition is substantially unchanged over a period of about 5 years.

37. A method of collecting a blood sample from a patient, the method comprising:
providing a container having an internal volume capable of receiving a blood sample;
loading a predetermined amount of an anti-coagulant powder into the internal volume of the container, the anti-coagulant powder comprising a heparin-bulking agent composition having a heparin component intermixed with at least one bulking agent component, wherein the free-flowing powder comprises a plurality of particles having an $X_{10}$ and $X_{90}$ value particle size distribution range between about 35 microns and about 400 microns, and wherein the heparin component comprises about 3% to about 40% by weight of a solid content of each of the plurality of particles of the heparin-bulking agent composition and the bulking agent comprises about 60% to about 97% by weight of the solid content of each of the plurality of particles of the heparin-bulking agent composition;
drawing the blood sample from the patient into the internal volume of the container; and
allowing the anti-coagulant powder to dissolve within the blood sample, wherein the predetermined amount of the free-flowing powder is readily dissolvable within the blood sample in under 10 seconds.

38. The method of claim 37, wherein the heparin component is a heparin salt chosen from lithium, sodium, calcium, zinc or combinations thereof.

39. The method of claim 38, wherein the bulking agent is a water soluble material selected from the group consisting of mannitol, trehalose, raffinose, sorbitol, sucrose, lactose, polyvinylpyrollidone, and combinations thereof.

40. The method of claim 39, wherein the container is a blood sample collection tube, a syringe, or a vacuum tube.

41. The method of claim 37, wherein the anti-coagulant powder is capable of being dissolved within the blood sample without agitation of the container.

42. The method of claim 37 further comprising inserting at least a portion of the blood sample collected into a blood analyzer for a blood gas analysis.

\* \* \* \* \*